(12) United States Patent
Konoike et al.

(10) Patent No.: US 6,479,671 B1
(45) Date of Patent: Nov. 12, 2002

(54) PROCESS FOR PRODUCING OPTICALLY ACTIVE CHROMENE DERIVATIVE

(75) Inventors: Toshiro Konoike, Amagasaki (JP); Tadahiko Yorifuji, Osaka (JP); Shoji Shinomoto, Osaka (JP); Yutaka Ide, Osaka (JP); Takashi Ohya, Osaka (JP); Ken-ichi Matsumura, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/622,283

(22) PCT Filed: Feb. 16, 1999

(86) PCT No.: PCT/JP99/00650

§ 371 (c)(1),
(2), (4) Date: Aug. 15, 2000

(87) PCT Pub. No.: WO99/42459

PCT Pub. Date: Aug. 26, 1999

(30) Foreign Application Priority Data

Feb. 18, 1998  (JP) ............................................. 10-035296

(51) Int. Cl.[7] ...................... C07D 311/30; C07D 335/06
(52) U.S. Cl. ........................... 549/23; 549/28; 549/400; 549/401
(58) Field of Search ........................... 549/23, 28, 400, 549/401

(56) References Cited

U.S. PATENT DOCUMENTS 4,665,202 A  5/1987  Rimbault et al.

FOREIGN PATENT DOCUMENTS

| JP | A6149581 | 8/1985 |
| WO | A1-9808836 | 3/1998 |

OTHER PUBLICATIONS

Indian J. Chem., vol. 8, No. 5, pp. 472–473 (1970).
Tetrahedron, vol. 46, No. 8, pp. 3029–3036 (1990).
Loncar et al., Croatica Chemica Acta, vol. 66, No. 1, pp. 209–216 (1993).
H. P. S. Chawla et al, Indian J. Chem., vol. 8, May 1970, pp. 472–473.
S. T. Saengchantara et al, Tetrahedron, vol. 46, No. 8, pp. 3029–3036, 1990.

*Primary Examiner*—T. A. Solola
(74) *Attorney, Agent, or Firm*—Birch, Stewart, Kolasch & Birch, LLP

(57) ABSTRACT

A process for producing a compound of the formula (II):

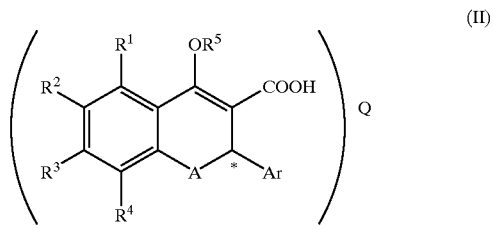

(wherein $R^1$, $R^2$, $R^3$ and $R^4$ are each independently hydrogen, alkyl, alkoxy or the like, $R^5$ is alkyl or alkoxyalkyl, A is O or S, Ar is aryl or the like, * represents the position of an asymmetric carbon atom and that the compound is the (R) or (S) isomer and Q is an optical resolution reagent)

comprising isolating the compound as crystals from a solution or suspension containing the compound of the formula (II) (wherein * represents that the compound is the (R) or (S) isomer or a mixture thereof and the other symbols are the same as the above).

2 Claims, No Drawings

PROCESS FOR PRODUCING OPTICALLY ACTIVE CHROMENE DERIVATIVE

This application is the national phase under 35 U.S.C. §371 of PCT International Application No. PCT/JP99/00650 which has an International filing date of Feb. 16, 2000, which designated the United States of America.

TECHNICAL FIELD

The present invention relates to a process for producing optically active chromene derivatives useful as a medicament or an intermediate thereof.

BACKGROUND ART

When a compound having some biological activity has an asymmetric center in the molecule, each enantiomer sometimes has a very different property. For example, even if one of enantiomers has a useful biological activity, the other may be inactive or induce side effects. Thus, optical resolution of racemates is very important to the development of medicaments.

The optical resolution methods of racemates are classified into a direct method and an indirect method. In the direct method, a racemate is directly resoluted into optically active compounds and the examples are preferential crystallization, gas chromatography, thin layer chromatography, HPLC and the like. In the indirect method, a racemate is reacted with an optically active reagent (optical resolving agent) to give diastereomers which are separated based on the difference of their physical properties, followed by removing the optically active reagent to give an optically active compound.

For example, a racemate (±)-A reacts with a proper optical resolving agent such as (+)-B to produce diastereomers (+)-A·(+)-B and (−)-A·(+)-B. Each diastereomer has a different physical property based upon which they can be separated by a certain method. When the separation is industrially performed, a recrystallization method is especially preferable, wherein one low-soluble diastereomeric salt only crystallizes while the other remains in a mother liquor owing to difference of their solubilities. Usually a resolution condition may be selected so that the diastereomeric salt containing an desired enantiomer crystallizes with high yield and utmost optical purity. After taking out the crystal, the diastereomeric salt containing an unnecessary enantiomer remains in the mother liquor. Removal of the optical resolving agent (+)-B from the diastereomeric salt separated as crystals and the diastereomeric salt in the mother liquor gives (+)-A and (−)-A, respectively.

However, the known optical resolution is not always effective regardless of the direct or indirect method, because the objective enantiomer can not be obtained with over 50% yield. For improving the yield close to theoretical 100%, the unnecessary enantiomer remaining after the resolution needed to be collected and be converted into the objective enantiomer.

The isolation and racemization of enantiomers of chromene compounds are described in Croatica Chemica Acta Vol. 66, No. 1, pp. 209–216(1993). But in the article, the enantiomer was separated by liquid chromatography and the present invention is not suggested at all.

DISCLOSURE OF INVENTION

The present invention provides a process for producing a compound of the formula (II):

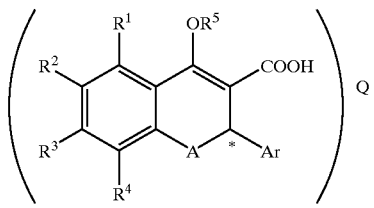

wherein $R^1$, $R^2$, $R^3$ and $R^4$ are each independently hydrogen, hydroxy, halogen, optionally substituted alkyl (wherein the substituent is halogen, hydroxy, cycloalkyl, carboxy, alkoxycarbonyl, alkoxy, alkoxyalkyloxy, acyl, alkylenedioxy, amino, alkylamino, aryl or heterocyclyl), optionally substituted alkenyl wherein the substituent is the same as the above, optionally substituted alkynyl wherein the substituent is the same as the above, optionally substituted cycloalkyl wherein the substituent is the same as the above, optionally substituted alkoxy wherein the substituent is the same as the above, optionally substituted alkenyloxy wherein the substituent is the same as the above, optionally substituted alkynyloxy wherein the substituent is the same as the above, optionally substituted cycloalkoxy (wherein the substituent is alkyl, alkenyl, halogen, hydroxy, cycloalkyl, carboxy, alkoxycarbonyl, alkoxy, alkoxyalkyloxy, acyl, amino, alkylamino, alkylenedioxy, aryl or heterocyclyl), optionally substituted acyloxy (wherein the substituent is halogen, hydroxy, cycloalkyl, carboxy, alkoxycarbonyl, alkoxy, alkoxyalkyloxy, acyl, alkylenedioxy, amino, alkylamino, aryl or heterocyclyl), or optionally substituted amino (wherein the substituent is alkyl, cycloalkyl, aryl or acyl), $R^5$ is alkyl or alkoxyalkyl, A is O or S, Ar is optionally substituted aryl (wherein the substituent is alkyl, alkenyl, halogen, hydroxy, cycloalkyl, carboxy, alkoxycarbonyl, alkoxy, alkoxyalkyloxy, acyl, alkylenedioxy, amino, alkylamino, aryl or heterocyclyl),

* represents the position of an asymmetric carbon atom and that the compound is the (R) or (S) isomer and Q represents an optically active reagent (hereinafter referred to as Compound (II)), comprising isolating the Compound (II) as crystals from a solution or suspension containing Compound (II) (wherein * represents the position of an asymmetric carbon atom and that the compound is the (R) or (S) isomer or a mixture thereof and the other symbols are the same as the above).

The present invention provides the above-mentioned process wherein the above Compound (II) (wherein * represents the position of an asymmetric carbon atom and that the compound is the (R) or (S) isomer or a mixture thereof and the other symbols are the same as the above) is contained in a mother liquor which is left after Compound (II) (wherein * represents the position of an asymmetric carbon atom and that the compound is the (R) or (S) isomer and the other symbols are the same as the above) is isolated as crystals from a solution or suspension containing a compound of the formula (III):

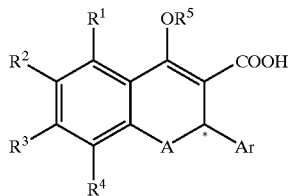

(wherein * represents the position of an asymmetric carbon atom and that the compound is a mixture of the (R) and (S) isomers and the other symbols are the same as the above) (hereinafter referred to as Compound (III)) and an optically active reagent Q.

The present invention provides a process for producing Compound (II) (wherein * represents the position of an asymmetric carbon atom and that the compound is the (R) or (S) isomer and the other symbols are the same as the above) comprising further subjecting Compound (II) (wherein * represents the position of an asymmetric carbon atom and that the compound is the (R) or (S) isomer or a mixture thereof and the other symbols are the same as the above), which is contained in a mother liquor left after isolating Compound (II) (wherein * represents the position of an asymmetric carbon atom and that the compound is the (R) or (S) isomer and the other symbols are the same as the above) in any of the above processes, to any of the above processes.

The present invention provides a process for producing a compound of the formula

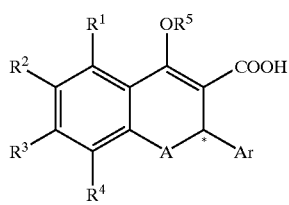

(wherein * represents the position of an asymmetric carbon atom and that the compound is the (R) or (S) isomer and the other symbols are the same as the above) (hereinafter referred to as Compound (I)) comprising removing an optically active reagent Q from Compound (II) (wherein * represents that the compound is of the same configuration as above Compound (I) and the other symbols are the same as the above) obtained by any one of the above processes.

The present invention provides a process for producing a compound of the formula (α):

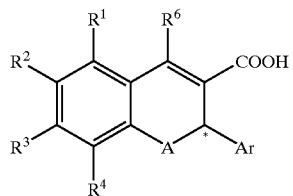

(wherein * represents the position of an asymmetric carbon atom and that the compound is the (R) or (S) isomer and the other symbols are the same as the above) (hereinafter referred to as Compound (α)) by the following steps:

1) A step for obtaining a compound of the formula (II):

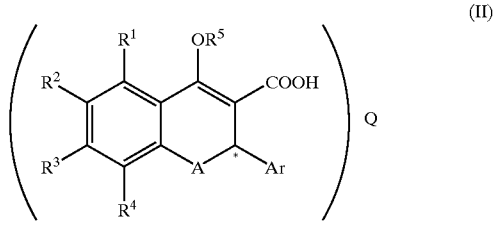

(wherein * represents the position of an asymmetric carbon atom and that the compound is of the same configuration as above Compound (α) and the other symbols are the same as the above)
and a mother liquor by isolating above Compound (II) as crystals from a solution or suspension containing a compound of the formula (III):

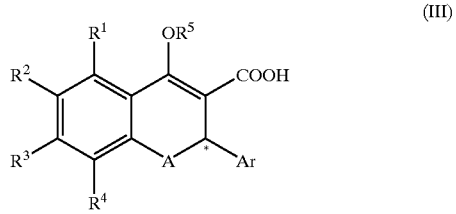

(wherein * represents the position of an asymmetric carbon atom and that the compound is a mixture of the (R) and (S) isomers and the other symbols are the same as the above) and an optically active reagent Q, 2) A step for isomerizing Compound (II) (wherein * represents the position of an asymmetric carbon atom and that the compound is the (R) or (S) isomer or a mixture thereof and the other symbols are the same as the above) in the above-mentioned mother liquor, to isolate Compound (II) (wherein * represents the position of an asymmetric carbon atom and that the compound is of the same configuration as above Compound (α) and the other symbols are the same as the above) as crystals and to obtain the left mother liquor, 3) A step for subjecting the mother liquor obtained in the above Step 2) to the additional step 2), if necessary, 4) A step for obtaining a compound of the formula (I):

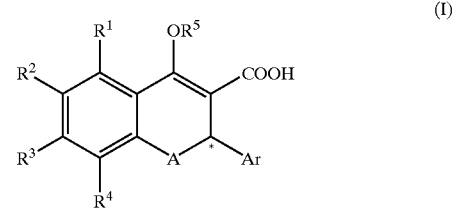

(wherein * represents the compound is of the same configuration as the compound of the above formula (α) and the other symbols are the same as the above) by removing an optically active reagent Q from the compound obtained in the above step 1), 2) or 3), 5) A step for reacting Compound (I) with a Grignard reagent $R^6$—MgX (wherein each symbol is the same as the above) while maintaining the asymmetric configuration.

The present invention provides a compound of the formula (II):

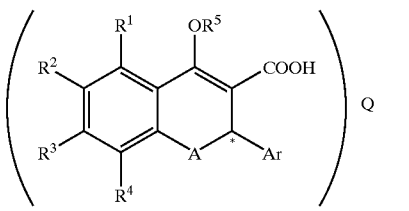

wherein * represents the position of an asymmetric carbon atom and that the compound is the (R) or (S) isomer and the other symbols are the same as the above and a compound of the formula (I):

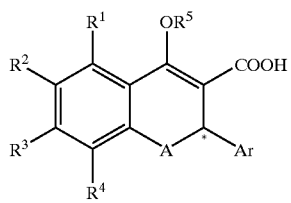

wherein * represents the position of an asymmetric carbon atom and that the compound is the (R) or (S) isomer and the other symbols are the same as the above.

BEST MODE FOR CARRYING OUT THE INVENTION

The preferable examples of Compounds (I), (II) and (III) are those wherein each substituent is as follows:

1) a compound wherein $R^1$, $R^2$, $R^3$ and $R^4$ are each independently hydrogen, optionally substituted alkyl (wherein the substituent is cycloalkyl, alkoxy, alkoxyalkyloxy, alkylenedioxy, aryl or heterocyclyl) or optionally substituted alkoxy (wherein the substituent is cycloalkyl, alkoxy, alkoxyalkyloxy, alkylenedioxy, aryl or heterocyclyl),
2) a compound wherein $R^1$ is hydrogen,
3) a compound wherein $R^2$ is C1–C6 alkoxy, preferably C3–C6 alkoxy, most preferably isopropyloxy,
4) a compound wherein $R^3$ is hydrogen,
5) a compound wherein $R^4$ is hydrogen,
6) a compound wherein $R^5$ is C1–C7 alkyl, preferably C1 or C3–C7 alkyl, most preferably methyl,
7) a compound wherein A is O,
8) a compound wherein Ar is phenyl optionally substituted with C1 or C2 alkylenedioxy, preferably benzo[1,3]dioxol-5-yl, or
9) a compound wherein $R^1$, $R^2$, $R^3$ and $R^4$ are each independently hydrogen, C3–C6 alkyl or C3–C6 alkoxy, $R^5$ is alkyl or alkoxyalkyl, A is O and Ar is benzo[1,3]dioxol-5-yl, preferably $R^1$ is hydrogen, $R^2$ is isopropyloxy, $R^3$ and $R^4$ are hydrogen, $R^5$ is methyl, A is O and Ar is benzo[1,3]dioxol-5-yl.

In the present specification, the term "halogen" includes fluorine, chlorine, bromine and iodine.

The term "alkyl" includes straight or branched chain alkyl of C1–C10, preferably C1–C7. When $R^1$–$R^4$ are each "alkyl" or "optionally substituted alkyl", alkyl are preferably C3–C6 alkyl. The "alkyl" of $R^5$ is preferably C1 or C3–C7 alkyl. Compound (I) wherein $R^5$ is C1 alkyl can be preferably used as an immediate for Compound (α), and Compound (I) wherein $R^5$ is C3–C7 alkyl has a potent endothelin antagonistic activity.

Examples of "alkyl" include methyl, ethyl, n-propyl, isopropyl, n-butyl, isobutyl, sec-butyl, tert-butyl, n-pentyl, isopentyl, neopentyl, hexyl, isohexyl, heptyl, isoheptyl, octyl, isooctyl, nonyl, decyl and the like. The alkyl parts of "alkylamino", "alkoxyalkyl" and "alkyl-substituted heterocyclyl" are the same as the above. A preferable example of "alkylamino" is dialkylamino.

The term of "cycloalkyl" includes cyclic alkyl of C3–C7, preferably C3–C6, more preferably C3–C5. For example, cyclopropyl, cyclobutyl, cyclopentyl, cyclohexyl, cycloheptyl and the like are included.

The cycloalkyl part of "cycloalkoxy" is the same as the above "cycloalkyl".

The term "alkoxy" includes straight or branched chain alkoxy of C1–C10, preferably C1–C7. Examples of "alkoxy" include methoxy, ethoxy, n-propoxy, isopropoxy, n-butoxy, isobutoxy, sec-butoxy, tert-butoxy, n-pentyloxy, isopentyloxy, neopentyloxy, n-hexyloxy, isohexyloxy and the like. When each of $R^1$–$R^4$ represents "alkoxy" or "optionally substituted alkoxy", the alkoxy is preferably C3–C6. When $R^5$ represents "alkoxyalkyl", the alkoxy is preferably methoxy.

The alkoxy parts of "alkoxycarbonyl", "carboxyalkoxy" and "alkoxyalkyloxy" are the same as the above. The alkoxy parts of in "alkoxyalkyl" is the same as the above and methoxymethyl is preferable.

The term "acyl" includes straight or branched chain acyl derived from aliphatic carboxylic acid of C1–C10, preferably C1–C8, more preferably C1–C6 and the examples are formyl, acetyl, propionyl, butylyl, isobutylyl, valeryl, pivaloyl, hexanoyl and the like.

The acyl part of "acyloxy" is the same as the above "acyl".

The term "alkylenedioxy" includes —O(CH$_2$)nO— wherein n is an integer of 1 to 3, and preferably n is 1.

The term "aryl" includes phenyl, naphthyl, anthryl, indenyl, phenanthryl and the like and phenyl is preferable.

The term "heterocyclyl" includes saturated or unsaturated 3- to 7-membered, preferably 5- to 7-membered heterocyclyl which contains at least one of hetero atoms arbitrarily selected from the group of O, S and N and which may be fused with benzene ring. The heterocyclyl may bond as a substituent at any possible position in the ring.

Examples of the heterocyclyl include non-aromatic heterocyclyl such as oxiranyl, dioxanyl, thiiranyl, dioxolanyl, oxathiolanyl, azetidinyl, pyrrolidinyl, pyrrolinyl, imidazohdinyl, imidazolinyl, pyrazolidinyl, pyrazolinyl, piperidinyl, piperazinyl, morpholinyl, dihydrobenzofuryl (e.g., 2,3-dihydro-5-benzofuryl, 2,3-dihydro-6-benzofuryl and the like), aromatic heterocycle such as pyrrolyl (e.g., 1-pyrrolyl), indolyl (e.g., 2- or 6-indolyl), carbazolyl (e.g., 3-carbazolyl), imidazolyl (e.g., 1-imidazolyl), pyrazolyl (e.g., 3-pyrazolyl), benzimidazolyl (e.g., 2-benzimidazolyl), indazolyl (e.g., 3-indazolyl), pyridyl (e.g., 3-pyridyl or 4-pyridyl), quinolyl (e.g., 8-quinolyl), isoquinolyl (e.g., 3-isoquinolyl), pyrimidinyl (e.g., 4-pyrimidinyl), pyrazinyl (e.g., 2-pyradinyl), isoxazolyl (e.g., 4-10 isoxazolyl), oxazolyl (e.g., 2-oxazolyl), furyl (e.g., 2-furyl or 3-furyl), benzothienyl (e.g., 1-benzothiophene-2-yl, 2-benzothiophen-1-yl) and the like.

The term "alkenyl" includes straight or branched chain alkenyl of C2–C10, preferably C2–C8, more preferably C2–C6. Examples are vinyl, propenyl, isopropenyl, butenyl, pentenyl, hexenyl, heptenyl, octenyl, nonenyl, decenyl and the like. These have at least one double bond at any possible position.

The alkenyl part of "alkenyloxy" is the same as the above "alkenyl".

The term "alkynyl" includes straight or branched chain alkynyl of C2–C10, preferably C2–C8, more preferably C2–C6, which was exemplified by ethynyl, propynyl, butynyl, pentynyl, hexynyl, heptynyl, octynyl, nonyl, decynyl and the like. These have at least one triple bond and may have a double bond at any possible position.

The alkynyl part of "alkynyloxy" is the same as the above "alkynyl".

A process for producing optically active chromene derivatives of the present invention is as follows.

1) Fractional Recrystallization
Compound (II):

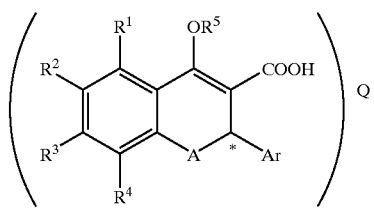

(wherein * represents the position of an asymmetric carbon atom and that the compound is the (R) or (S) isomer and the other symbols are the same as the above) and a mother liquor are obtained by isolating Compound (II) as crystals from a solution or suspension containing Compound (III):

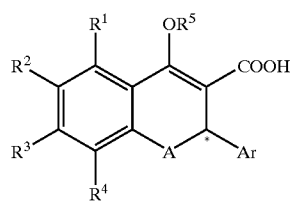

(wherein * represents that the compound is a mixture of the (R) and (S) isomers and the other symbols are the same as the above)

and the optically active reagent Q.

The optically active reagent Q used in this step may be that generally used as a basic optical resolving agent. The optically active reagent Q reacts with Compound (III) to produce Compound (II). Compound (II) is a mixture of two kinds of diastereomeric salts. One is the salt of (R)-Compound (III) with optically active reagent Q and the other is the salt of (S)-Compound (III) with optically active reagent Q. These two kinds of diastereomeric salts have different physical properties and the resolution by the properties is possible. A preferable industrial method for resolving the diastereomeric salts is a recrystallization method by utilizing the difference of solubility.

A preferable optically active reagent Q is that which satisfies the following conditions, i.e., optical purity of the reagent is as high as possible, a large quantity of the reagent is easily available, the reagent is a cheap organic base, both isomers of the reagent are available, the difference of solubility between the (R) isomer and (S) isomer of obtained Compound (II) is large and the like. Among them, a proper resolving agent, which can most efficiently crystallize Compound (II) containing the objective isomer of Compound (III), may be selected. Exemplified are norephedrine, brucine, strychnine, cinchonine, cinchonidine, quinine, quinidine, ephedrine, L-(+)-lysine, L-(+)-arginine, dehydroabietylamine, 1-methylbenzylamine, 1-methyl-p-nitrobenzylamine, 1-ethylbenzylamine, 1-(p-tolyl)ethylamine, 1-phenyl-2-(p-tolyl)ethylamine, 1-(1-naphtyl)ethylamine, 1-(2-naphtyl)ethylamine, erythro-2-amino-1,2-diphenylethanol, cis-2-(benzylamino)cyclohexanemethanol, threo-2-amino-1-(p-nitrophenyl)-1,3-propanediol, threo-2-(N,N-dimethylamino)1-(p-nitrophenyl)-1,3-propanediol and the like. The preferable examples are norephedrine, 1-methylbenzylamine, cinchonine and quinidine.

These may be used about 0.5 to 1.5 equivalent, preferably about 0.8 to 1.2 equivalent, and most preferably about 1 equivalent, to Compound (III).

A preferable solvent used in this step is that wherein two kinds of diastereomeric salts of Compound (II) can easily be resoluted by recrystallization, as mentioned above for the optically active reagent Q. Examples include water, lower alcohol, acetate ester (such as methyl acetate, ethyl acetate and the like), acetone, acetonitrile and mixture thereof. Preferable examples are ethyl acetate, lower alcohol (such as methanol, ethanol, n-propanol, isopropanol and the like), acetone and a mixture thereof, more preferable are lower alcohol, and most preferable are methanol and ethanol. The preferable solvents depend on the conditions such as the structure of Compound (III), type of the optically active reagent and the like. A proper solvent may appropriately be selected for the combination with Compound (III) and the reagent. Compound (III) and the optically active reagent Q are added into the above-mentioned solvent around room temperature to boiling point of the solvent, preferably around room temperature, to obtain a solution or suspension.

Alternatively, the solvent may be added to previously produced Compound (II) (wherein * represents the position of an asymmetric carbon atom and that the compound is the (R) or (S) isomer or a mixture thereof and the other symbols are the same as the above) around room temperature to boiling point of the solvent, preferably around room temperature, to obtain a solution or suspension. The previously produced Compound (II) may be the (R) or (S) isomer or a mixture thereof. When the (R) isomer is previously produced, the (S) isomer can be obtained and when the (S) isomer is previously produced, the (R) isomer can be obtained by the process of the present invention. Compound (II) is preferably a mixture of the (R) and (S) isomers to easily obtain the objective compound.

Preferably about 50% of Compound (II) in this solution or suspension is that containing the objective enantiomer (III). If the ratio of Compound (II) containing the objective enantiomer (III) is 50% or less, Compound (II) may be previously isomerized in the solution or suspension by the following process, so as to increase the ratio to about 30 to 50%, preferably 40 to 50%, more preferably 45 to 50%, whereby the next step of the reaction can preferably be carried out.

From thus obtained solution or suspension, Compound (II) (wherein * represents the position of an asymmetric carbon atom and that the compound is the (R) or (S) isomer) is isolated as crystals by the usual method. For example, the solution or suspension is allowed to stand or stirred at room temperature or under ice-cooling, to crystallize Compound (II) (wherein * represents that the compound is the (R) or (S) isomer), which can be isolated by filtration or the like in one step. Otherwise, the precipitated crystals may be isolated in order to continually repeat the operations of isomerization, crystallization and separation. Seed crystals of the objective diastereomeric salt are preferably added in the solution or suspension before the crystallization.

Optical purity of the isolated crystals is determined by HPLC or optical rotation or the like, if necessary. In the case that the optical purity does not reach the desired level, recrystallization may be repeated with the above-mentioned solvent, which may be same or different kind in each recrystallization.

Among Compound (II) obtained by this process, 75% or more, preferably 85% or more, more preferably 95% or more of them contains the objective isomer (III).

2) Isomerization

After Compound (II) containing the objective isomer (III) is isolated by the above process, much of Compound (II) containing another unnecessary isomer (III) remains in the mother liquor. Generally, further obtaining only the objective Compound (II) from the mother liquor is very difficult. In the present invention process, however, repeated operations of isomerization, crystallization and separation, if necessary, can give Compound (II) containing the objective Compound (III) again.

The mother liquor may directly be used in the isomerization. If the solvent is too much or too little, the volume can suitably be adjusted by removing or adding the solvent, or by adding a proper solvent after removing the solvent. The additional solvent may be the same kind as or different from the removed solvent.

Isomerization can be carried out under heating at room temperature to boiling point of the solvent for several minutes to several tens hours. The reaction can be carried out preferably around room temperature and more preferably around the boiling point of the solvent for the short-time reaction.

The reaction may be terminated at the point that the ratio of Compound (II) containing the objective isomer (III) reaches about 30 to 50%, preferably about 40 to 50%, more preferably about 45 to 50% through HPLC determination, then the above-mentioned operation is repeated to isolate only the objective diastereomeric salt Compound (II) from the reaction mixture. For example, the reaction mixture may be refluxed in methanol for one to several hours.

When the operations of the above-mentioned isomerization and recrystallization are repeated several times if necessary, the yield of the objective diastereomeric salt Compound (II) theoretically reaches near 100%. The frequency of repeating isomerization and recrystallization may be determined according to the balance of the desired purity and yield because the purity of the obtained crystals sometimes decreases depending on repeating the operation. For example, the crystals with the final purity 90% or more can be obtained at about 70 to 90% yield. Even the purity is not 100%, it sometimes can be increased by recrystallizing and purifying Compound (I) synthesized by the following method.

3) Removing the Optically Active Reagent Q

Compound (I) can be obtained by removing the optically active reagent Q from Compound (II) obtained by the above-mentioned method.

Examples of the method for the removing is hydrolysis and the like. For example, Compound (I) is added to an aqueous solution of mineral acid such as hydrochloric acid, dilute sulfuric acid, phosphoric acid or the like with stirring under ice-cooling or at room temperature and extracted with a proper solvent to remove the optically active reagent. The reaction is preferably carried out after adjusting the pH to 3 to 5, preferably about 4, with phosphate or the like. The extracted Compound (I) may be purified by recrystallization or the like after the solvent is removed under reduced pressure or the like, if necessary.

4) Recovery of the Optically Active Reagent Q

The optically active reagent Q can be recovered and reused. For example, the aqueous layers after liberating Compound (I) by the above-mentioned method are collected and a mineral base such as sodium hydroxide, potassium hydroxide or the like is added thereto under ice-cooling to liberate the optically active reagent Q. The resultant solution is extracted with a proper solvent, which is removed under reduced pressure, and the residue is purified by distillation, recrystallization or the like. Thus-obtained optically active reagent Q can be reused.

5) Conversion to Compound (α) from Compound (I)

Compound (I) itself has an endothelin receptor antagonistic activity and it is useful also as an intermediate of Compound (α), the salt or hydrate thereof having a more potent endothelin receptor antagonistic activity:

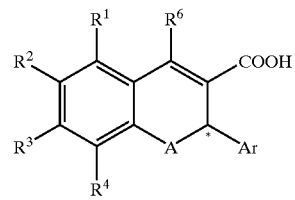

(α)

(wherein $R^6$ is optionally substituted alkyl (wherein the substituent is halogen, hydroxy, cycloalkyl, alkoxy, alkoxyalkyloxy, alkylenedioxy, aryl or heterocyclyl) or optionally substituted aryl (wherein the substituent is alkyl, alkenyl, halogen, cycloalkyl, alkoxy, alkoxyalkyloxy, alkylenedioxy, aryl or heterocyclyl), * represents the position of an asymmetric carbon atom and that the compound is the (R) or (S) isomer and the other symbols are the same as the above).

Compound (α) can be produced by the procedure described in PCT/JP97/02916 from optically active Compound (I) obtained by the above-mentioned method. For example, Compound (I) is reacted with a Grignard reagent $R^6$—MgX (wherein $R^6$ is optionally substituted alkyl (wherein the substituent is halogen, hydroxy, cycloalkyl, alkoxy, alkoxyalkyloxy, alkylenedioxy, aryl or heterocyclyl) or optionally substituted aryl (wherein the substituent is alkyl, alkenyl, halogen, cycloalkyl, alkoxy, alkoxyalkyloxy, alkylenedioxy, aryl or cycloalkyl) and X is halogen) which is prepared by the usual method, to give the objective Compound (α) maintaining the asymmetric configuration. The Grignard reagent may be used about 2 equivalent, preferably about 3 equivalent, more preferably about 4 equivalent per 1 equivalent of Compound (I). Anhydrous ethereal solvent such as tetrahydrofuran, ether or the like can usually be used as a solvent. The reaction temperature may usually be −50° C. to room temperature.

Preferable examples of Compound (α) are shown below.
1) A compound wherein $R^6$ is optionally substituted aryl wherein the substituent is alkyl, alkoxy or alkylenedioxy, preferably a compound wherein $R^6$ is phenyl wherein the substituent is alkyl, alkoxy or alkylenedioxy.
2) A compound wherein the $R^1$, $R^2$, $R^3$ and $R^4$ is hydrogen, C3–C6 alkyl or C3–C6 alkoxy, A is O, Ar is benzo[1,3]dioxol-5-yl and $R^6$ is optionally substituted aryl wherein the substituent is alkyl, halogen, alkoxy, carboxyalkoxy, alkylenedioxy, amino or alkylamino, preferably a compound wherein $R^1$ is hydrogen, $R^2$ is isopropyloxy, both of $R^3$ and $R^4$ are hydrogen, $R^5$ is methyl, A is O, Ar is benzo[1,3]dioxol-5-yl and $R^6$ is 4-methoxyphenyl.

Endothelin is considered to be associated with circulatory system diseases such as hypertension, pulmonary hypertension, stroke, acute renal insufficiency, stenocardia, cardiac insufficiency, myocardial infarction, renal ischemia, renal insufficiency, cerebral ischemia, cerebral infarction, cerebral edema, cerebrovascular spasm, and asthma, peripheral circulatory insufficiency (e.g., acute and chronic artery obstruction, obstructive arteriosclerosis, obstructive thromboangiitis, Raynaud's syndrome, diabetic cutaneous ulcer, diabetic neuropathy, diabetic vulnerary insufficiency, peripheral circulatory insufficiency of unknown etiology, subjective symptoms (e.g., pain, feeling of cold and shoulder stiffness) which are caused by a peripheral circulatory insufficiency, and the like). Therefore, Compound (I) and Compound (α) of the present invention are useful for treating and/or preventing these diseases.

Compound (III), a starting material for compounds of the present invention, can be produced by the method described in PCT/JP97/02916. For example, Compound (III) may be synthesized using Compound (IV) produced by the following method A or method B as a key intermediate.

Process for producing Compound (IV)

(wherein $R^7$ is formyl or $COOR^8$ (wherein $R^8$ is hydrogen or alkyl), Z is halogen, hydroxy or $OR^5$ and the other symbols are the same as the above)

Method A (VI→V→IV; Z is halogen or $OR^5$; A=O)

(Method A Step 1) (VI→V)

This step can be carried out by a method described in J. Org. Chem., 1970, 35(7), 2286. Condensation of Compound (VI) with aldehyde Ar—CHO (wherein Ar is the same as the above) in the presence of a base gives chromanon (V). Examples of the base include an inorganic base such as sodium hydroxide, potassium hydroxide, sodium hydride or an organic base such as potassium t-butoxide or piperidine. Alcohol such as methanol, t-butanol or the like, an ethereal solvent such as tetrahydrofuran, dioxane or the like, water, or mixture thereof can be used as a solvent. The starting compound (VI) is commercially available or prepared from a commercially available compound by a known method. Examples of Compound (VI) are ortho-hydroxyacetophenone, 2',3'-dihydroxyacetophenone, 2',4'-dihydroxyacetophenone, 2',5'-dihydroxyacetophenone, 2',6'-dihydroxyacetophenone, 2'-hydroxy-6'-propoxyacetophenone, 5'-cyclopropylmethyl-2'-hydroxyacetophenone, 5'-benzyloxy-2'-hydroxyacetophenone, 2'-hydroxy-5'-propoxyacetophenone, 2'-hydroxy-4'-propoxyacetophenone, 2'-hydroxy-3'-propoxyacetophenone, 2'-hydroxy-5'-isopropoxyacetophenone, 2'-hydroxy-5'-nitroacetophenone,

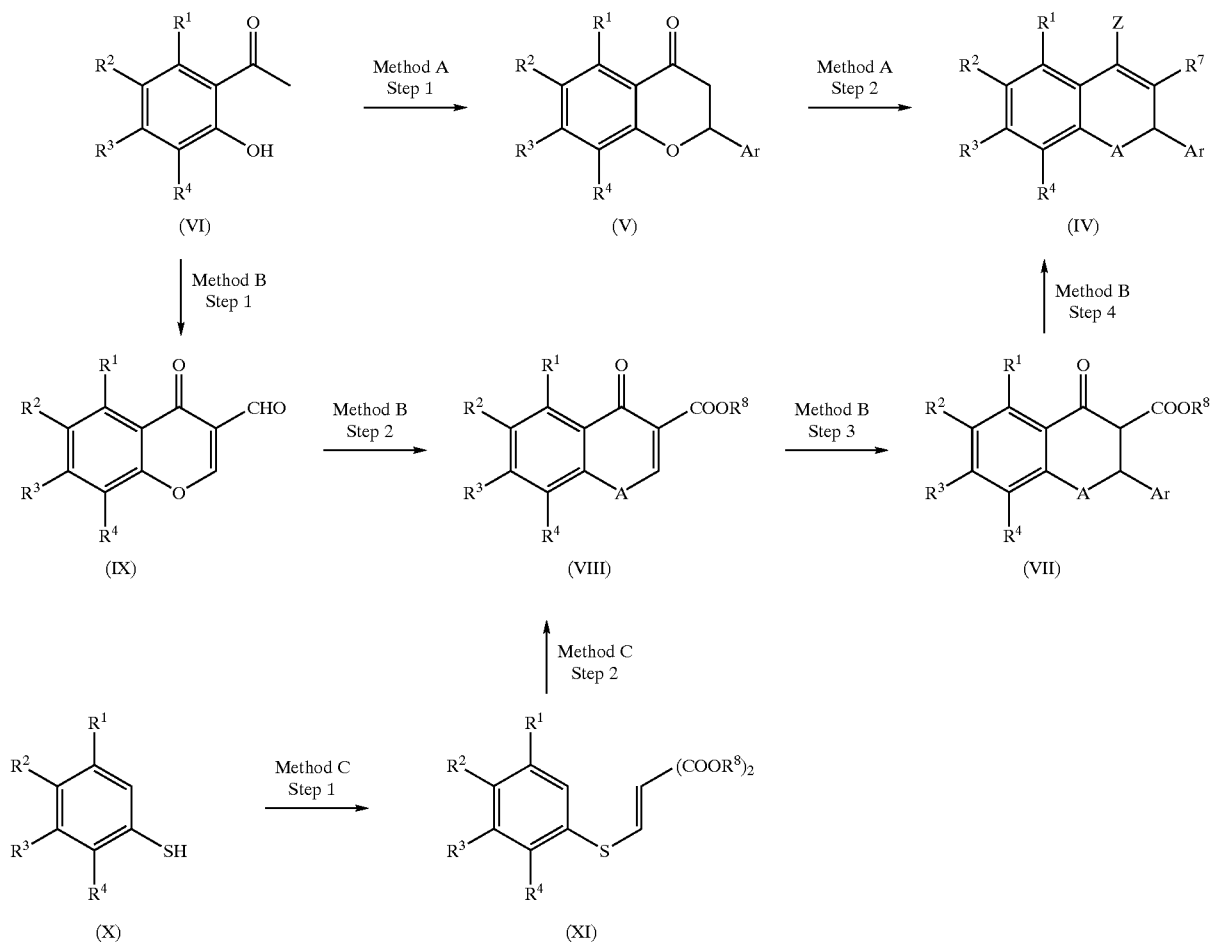

2'-hydroxy-3'-nitroacetophenone, 2'-hydroxy-5'-propoxy-3'-propylacetophenone, 2'-hydroxy-5'-isopropylacetophenone and the like.

(Method A Step 2) (V→IV)

This step is generally known as the Vilsmeier Reaction. When Compound (V) is reacted with N,N'-di substituted formamide such as dimethylformamide and a chlorinating agent such as phosphorous oxychloride, thionyl chloride or the like, Compound (IV) wherein Z is chlorine and $R^7$ is formyl can be obtained. When phosphorus tribromide is used in stead of the chlorinating agent, Compound (IV) wherein Z is bromine and $R^7$ is formyl can be obtained. This reaction may be carried out at −10° C. to 50° C.

When thus obtained Compound (IV) is reacted with an alkaline metal salt or an alkaline earth metal salt of alcohol, Compound (IV) wherein Z is $OR^5$ and $R^7$ is formyl can be obtained. The reaction may be carried out in a solvent such as methanol, dimethylformamide, tetrahydrofuran, 1,4-dioxane or the like at room temperature to refluxing temperature of the solvent.

Oxidation of Compound (IV) wherein $R^7$ is formyl can give Compound (IV) wherein $R^7$ is $COOR^8$ and $R^8$ is hydrogen. The oxidation may be carried out under usual oxidization conditions of aldehydes, and oxidation with a chlorite salt is particularly specifically preferable (Acta. Chem. Scand., 1973, 27(3), 888–890). Examples of the oxidizing agent are sodium chlorite, potassium chlorite and the like and these are usually used in the presence of sulfamic acid, dimethylsulfoxide, hydrogen peroxide, 2-methyl-2-butene or the like. A buffer such as sodium dihydrogen phosphate or the like can be added if necessary. Dichloromethane, chloroform, dichloroethane, dimethylsulfoxide, acetone, acetonitrile, water or mixture thereof can be used as a solvent. The reaction is usually carried out at 0 to 40° C.

Compound (IV) wherein $R^7$ is $COOR^8$ and $R^8$ is alkyl can be prepared from another Compound (IV) wherein $R^7$ is $COOR^8$ and $R^8$ is hydrogen by esterification in a usual manner.

Method B (VI→IX→VIII→VII→IV; $R^7=COOR^8$, A=O)

(Method B Step 1) (VI→IX)

This step can be carried out by the method described in Tetrahedron, 1974, 30, 3553–3561. Compound (IX) can be obtained by reacting Compound (VI) with N,N'-di substituted formamide such as dimethylformamide in the presence of phosphorous oxychloride or thionyl chloride or the like for a few hours to several tens hours, preferably 3 to 24 hours.

(Method B Step 2) (IX→VIII)

In this step, Aldehyde (IX) is oxidized to carboxyl Compound (VIII) wherein $R^8$ is hydrogen, followed by being converted into a corresponding ester Compound (VII) wherein $R^8$ is optionally substituted alkyl or optionally substituted aryl. The oxidation reaction may be carried out under usual conditions used for oxidizing aldehydes. Preferable examples are a method of light irradiation with N-bromosuccinimide in carbon tetrachloride (Synth. Commun., 1980, 10, 889–890) and a method of oxidizing with a chlorite in the presence of a chlorine scavenger (Acta. Chem. Scand., 1973, 27(3), 888–890). In the oxidation with a chlorite, sodium chlorite, potassium chlorite or the like can be used together with a chlorine scavenger such as sulfamic acid, dimethylsulfoxide, hydrogen peroxide, 2-methyl-2-buten or the like. A buffer such as sodium dihydrogen phosphate may be added if necessary. Dichloromethane, chloroform, dichloroethane, dimethylsulfoxide, acetone, acetonitrile, water or mixture thereof can be used as a solvent. The reaction may usually be carried out at 0 to 40° C.

(Method B Step 3) (VIII→VII)

This step is a process wherein a substituent Ar is introduced into the 2-position of ester Compound (VIII) and can be carried out by a similar method described in Org. Reaction, 1972, 19, 1.

A Grignard reagent Ar—MgX (wherein Ar is the same as the above and X represents halogen) is prepared by a standard method. Then, Ar—MgX is subjected to a 1,4-addition reaction with Compound (VIII) in the presence of a copper catalyst such as copper iodide to give Compound (VII). Tetrahydrofuran, ether or the like may be used as a solvent and tetrahydrofuran is preferable. Copper (I) iodide, copper (I) cyanide, copper (I) bromide-dimethylsulfide complex or the like can be used as a copper catalyst. The reaction may be usually carried out at room temperature to refluxing temperature of the solvent.

Compound (VII) may usually be a mixture of keto-enol tautomer formed by the ester group at 3-position and the carbonyl group at 4-position of the chromanone ring, as a results, it may be a stereoisomer of the 2- and 3-positions as well. In the above scheme, only one of possible structures is shown for convenience. The mixture of isomers can be used without further isolation and purification in the following Method B Step 4 and can also be used as intermediates for the synthesis of Compound (III) in the following Method a, b, c and d.

(Method B Step 4) (VII→IV)

In the present step, a leaving group Z is introduced into the 4-position of Compound (VII).

The reaction of Compound (VII) with tetrahalognomethane in the presence of triphenylphosphine is able to produce Compound (IV) wherein Z is halogen, $R^7$ is $COOR^8$ and $R^8$ is alkyl. For example, the reaction of Compound (VII) with carbon tetrachloride gives Compound (IV) wherein Z is chlorine, $R^7$ is $COOR^8$ and $R^8$ is alkyl. Chloroform, carbon tetrachloride, ether or the like can be used as a solvent. The reaction can be usually carried out at room temperature to refluxing temperature of the solvent.

Method C (X→XI→VI→II→VII→IV; Z=Halogen or Hydroxy, A=S)

(Method C Steps 1 and 2)

Compound (VIII) can be prepared by the known method described in WO91/11443 from Compound (X) as a starting material which is obtained in the usual method.

Method for Producing Compound (III)

Thus obtained intermediate (IV) or (VII) may be converted into Compound (III) by the following Method a, b, c or d.

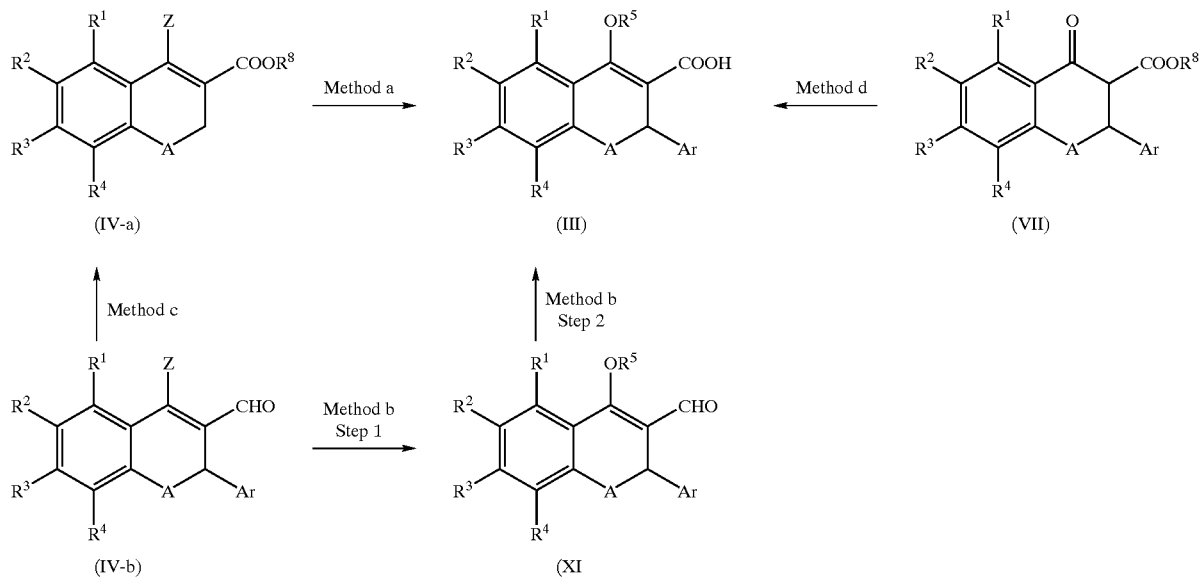

(wherein each symbol is the same as the above).

Method a (IV-a→III)

Compound (III) can be produced by a reaction of Compound (IV-a) wherein Z is halogen with an alkaline metal salt or alkaline earth metal salt of the corresponding alcohol. Tetrahydrofuran, dimethylformamide or the like is used as a reaction solvent. The reaction may usually be carried out at room temperature to 50° C.

Compound (IV-a) wherein $R^8$ is alkyl can be converted into compound wherein $R^8$ is hydrogen by hydrolysis with an acid or alkali after the above reaction. Hydrolysis may be carried out in the usual method and preferably with an inorganic base in water-alcohol or water-dimethylsulfoxide. For example, sodium hydroxide, lithium hydroxide, potassium hydroxide or the like can be used as an inorganic base. The reaction may be usually carried out under ice-cooling to refluxing temperature of the solvent.

Method b (IV-b→XI→III)

(Method b Step 1) (IV-b→XI)

Compound (XI) wherein $R^5$ is hydrogen can be produced by a reaction of Compound (IV-b) wherein Z is halogen with an alkaline metal salt or alkaline earth metal salt of the corresponding alcohol, which is the same method as the above Method a. Tetrahydrofuran, dimethylformamide, dimethylsulfoxide, the corresponding alcohol (e.g., methanol) or the like can used as a reaction solvent. The reaction may be usually carried out at room temperature to refluxing temperature of the solvent.

(Method b Step 2) (XI→III)

Compound (III) can be obtained by oxidation of the corresponding Formyl Compound (XI). The oxidation of formyl compound to carboxy compound can be carried out in a usual manner for oxidation of an aldehydes. Preferable examples are a method of light irradiation with N-bromosuccinimide in carbon tetrachloride (Synth. Commun., 1980, 10, 889–890) and a method of oxidizing with a chlorite in the presence of a chlorine scavenger (Acta. Chem. Scand., 1973,27(3), 888–890). In the oxidation with a chlorite, sodium chlorite, potassium chlorite or the like can be used with a chlorine scavenger such as sulfamic acid, dimethylsulfoxide, hydrogen peroxide, 2-methyl-2-buten or the like. A buffer such as sodium dihydrogen phosphate may be added if necessary. Dichloromethane, chloroform, dichloroethane, dimethylsulfoxide, acetone, acetonitrile, water or a mixture thereof can be used as a solvent. The reaction may be usually carried out at 0 to 40° C.

Method c (IV-b→IV-a→III)

Oxidation of formyl group in Compound (IV-b) wherein Z is halogen or $OR^5$ can give Compound (IV-a) wherein $R^8$ is hydrogen, Z is halogen or $OR^5$. The method for oxidation of formyl group to carboxy group is the same as the above Method b.

The objective Compound (III) can be produced by the above-mentioned Method a.

Method d (VII→III)

Compound (III) wherein $R^5$ is alkyl can be synthesized by reacting Compound (VII) wherein $R^8$ is alkyl with the corresponding alcohol in the presence of triphenylphosphine or tributylphosphine and dialkylazodicarboxylate (e.g., diethylazodicarboxylate) or tetraalkylazodicarboxamide (e.g., 1,1-(azodicarbonyl)dipiperidine, N,N, N',N'-tetramethylazodicarboxamide). This reaction may be carried out according to the method described in Synthesis 1981, 1, (Mitsunobu Reaction). The examples of preferable solvents are ethereal solvent such as tetrahydrofuran, benzene, toluene and the like. The reaction may be usually carried out at −15° C. to room temperature.

Compound (III) wherein $R^5$ is alkyl can be obtained by a reaction of Compound (VII) wherein $R^8$ is alkyl with a diazotization reagent such as diazomethane. The reaction may be carried out in a solvent such as alcohol (e.g., ethanol etc.), acetone, ether or tetrahydrofuran or mixture thereof at 0° C. to room temperature.

Compound (III) wherein $R^8$ is alkyl obtained by the above-mentioned method can be converted into Compound (III) wherein $R^8$ is hydrogen by hydrolysis at a proper stage in a series of the reactions.

If there is an interfering substituent at any position in a molecule in any of the above-mentioned reaction steps, the group may previously be protected by a method as explained in Protective Groups in Organic Synthesis; Johon Wiley & Sons: New York, 1991 and the like. The protecting group may be removed in a later proper step.

For example, if there is hydroxy or amino, a preferable protecting group is benzyl, acetyl, benzoyl and the like. When the protecting group is benzyl, it can be removed by catalytic hydrogenation. When the protecting group is acyl such as acetyl, benzoyl or the like, it can be removed by hydrolysis with sodium carbonate, potassium carbonate, sodium hydroxide, potassium hydroxide, lithium hydroxide or the like in a solvent such as a mixture of lower alcohol and water. Tetrahydrofuran, dioxane or the like may further be added to the mixture. Carbonyl group such as aldehyde or the like may be protected as acetal, ketal or the like, followed by deprotection by the hydrolysis. Compounds having a double bond can also be converted into a carbonyl derivative by oxidation such as hydroxylation, hydroboration, epoxidation and the like.

The present invention is further explained by the following Examples and Experiments, which are not intended to limit the scope of the present invention. HPLC analysis condition for determination of optical purification in Examples are as follows: Column: CHIRALCEL OJ-R(4.6× 150 mm) (Daisel Chemical Industries, Ltd.); Mobile Phase: acetonitrile-0.2 N phosphoric acid, potassium dihydrogen phosphate buffer (pH 2.2)=50:50; Flow rate 0.5 mL/min.; Detection: UV (286 nm).

EXAMPLES

Example 1

(Step 1) Synthesis of Compound (II-1: R-Salt) from Compound (III-1: Racemate)

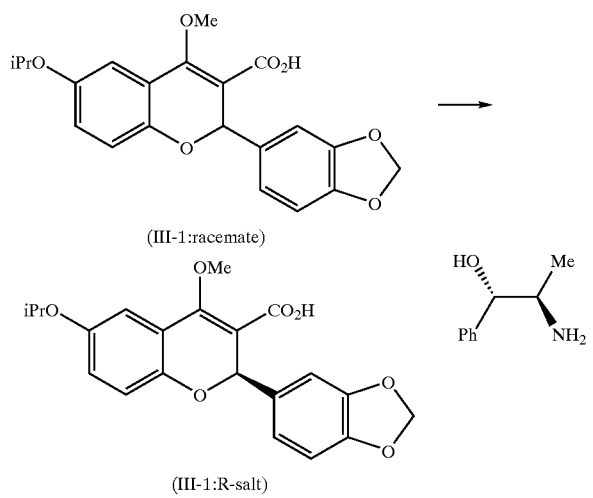

Compound (III-1: racemate) (327 g) was dissolved in ethyl acetate (3.27 L) and (1S, 2R)-(+)-norephedrine (129 g) was added to the solution. Seed crystals of Compound (II-1: R-salt) were added to the solution and the mixture was allowed to stand for 19 hours at room temperature. Then, the precipitates were filtered to isolate 217 g of crystals (R/S= 94/6). In methanol (2.17 L), 217 g of the crystals was dissolved with heating for 10 minutes, then acetonitrile (2.17 L) was added thereto and methanol was concentrated. Acetonitrile (1.74 L) was added to the slurry of the concentrated solution. After acetonitrile (1.0 L) was added to the slurry again, the solution was concentrated, then the precipitates were filtered.

(II-1: R-salt) 184 g (40%) (R/S=100/0); δH (d6-DMSO): 0.87(3H, d, J=6.6 Hz, amine-CH$_3$), 1.21 (6H, d, J=6.2 Hz, CH$_3$X2), 3.25–3.36 (1H, m, amine-CH), 3.89 (3H, s, OCH$_3$), 4.35–4.53 (1H, m, CH), 4.86 (1H, d, J=3.2 Hz, amine-H), 5.93 (2H, s, OCH$_2$O), 6.04 (1H, s, C2-H), 6.67–7.35 (11H, m, aromatic-H); Calcd. for C$_{21}$H$_{20}$O$_7$: C, 67.28; H, 6.21; N, 2.62 Found: C, 67.25; H, 6.27; N, 2.91. [α]$_D^{22}$+51.0±0.9 (c=1.0, MeOH).

(Step 2) Synthesis of Compound (I-1: R-Acid) from Compound (II-1: R-Salt)

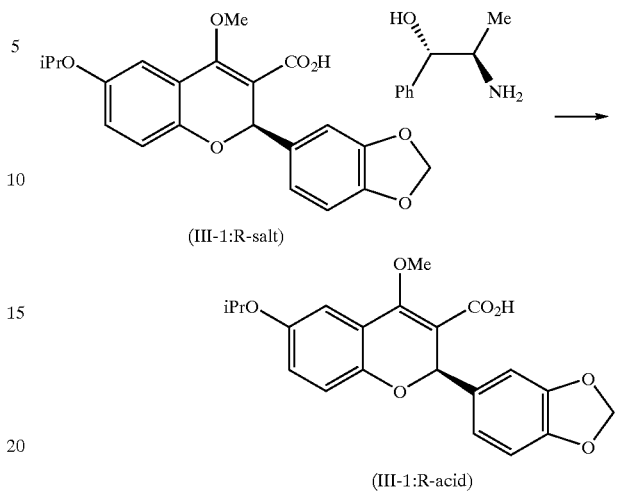

Compound (II-1: R-salt) (183 g) and ethyl acetate (1.83 L) were added to a 1 M aqueous solution of sodium dihydrogen phosphate (915 ml) under stirring. To the suspension, 10% aqueous solution of phosphoric acid (about 220 ml) was added at 20° C. and the pH was adjusted to 4.15 to dissolve Compound (II-1: R-salt). The ethyl acetate layer was separated, dried over anhydrous magnesium sulfate and concentrated under reduced pressure. Toluene was added to the obtained crystalline residue and the mixture was concentrated under reduced pressure to remove ethyl acetate, to give 149 g of Compound (I1: R-acid) as residue.

δH (CDCl$_3$): 1.30 (3H, d, J=6 Hz), 1.33 (3H, d, J=6 Hz), 4.01 (3H, s, OCH$_3$), 4.34–4.52 (1H, m, CH), 5.89 (2H, s, OCH$_2$O), 6.25 (1H, s, C2-H), 6.65–6.92 (6H, m, aromatic-H).

(Step 3) Synthesis of Compound (α-1) from Compound (I-1: R-Acid)

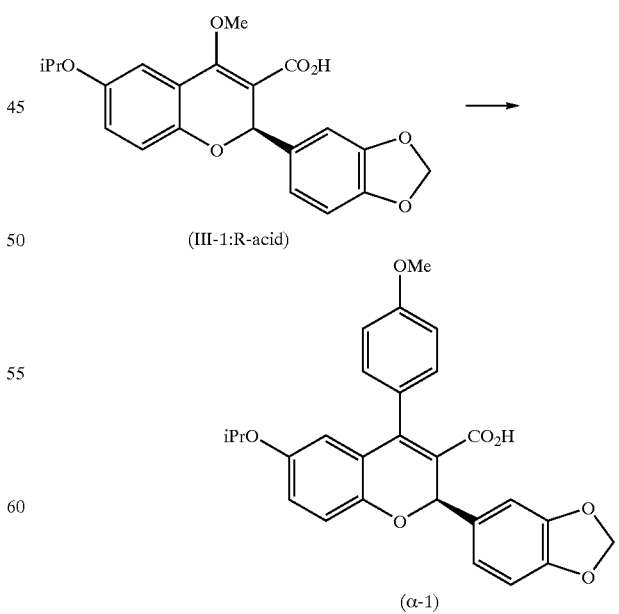

A solution of para-methoxyphenyl magnesium bromide in tetrahydrofuran (1 M 1.3 L) was added to a solution of 131 g of Compound (I1: R-acid) in anhydrous tetrahydrofuran anhydride (915 mL) at −35° C. for 30 minutes. The cool bath was immediately removed and the solution was allowed to warm and stirred at 5° C. for 2 hours to terminate the reaction. The reaction solution was poured into diluted hydrochloric acid and extracted with ethyl acetate. The extract was concentrated under reduced pressure, to which toluene was added and the mixture was extracted twice with 1 N solution of sodium hydroxide. The extracted aqueous layers were collected and the pH was adjusted to 2.95 with hydrochloric acid to extract Compound (α-1) with ethyl acetate. The ethyl acetate ester layer was washed with water, dried over anhydrous sodium sulfate anhydride and concentrated under reduced pressure. The concentrated residue was purified with aqueous methanol to give 147 g of Compound (α-1) (94%) as pale yellow crystals.

$\delta_H$ (CDCl$_3$): 1.15 (3H, d, J=6.2 Hz, CH$_3$), 1.18 (3H, d, J=6.2 Hz, CH$_3$), 3.87 (3H, s, OCH$_3$), 4.09–4.27 (1H, m, CH), 5.90 (2H, s, OCH$_2$O), 6.14 (1H, s, C2-H), 6.24–7.18 (10H, m, aromatic-H); mp 170–172° C. $[\alpha]_D^{22}$+176 (c=1.0, MeOH).

Example 2

Synthesis of (+)-2-(Benzo[1,3]dioxol-5-yl)-4-butyl-6-isopropyl-2H-chromen-3-carboxylic Acid (α-2)

Compound (α-2) was synthesized in the same manner as Example 1 Step 3 from Compound (I-1: R-acid) and n-butyl magnesium bromide.

mp 148–149° C.; $[\alpha]_D^{22}$+61.3 (c=1.00, MeOH) Calcd.for C$_{24}$H$_{26}$O$_6$: C, 70.23; H, 6.38 Found: C, 70.01; H, 6.43. $\delta_H$ (CDCl$_3$): 0.98 (3H, t, J=7.20 Hz), 1.30 (3H, d, J=6.0 Hz), 1.31 (3H, d, J=6.0 Hz), 1.38–1.73 (4H, m), 2.92–3.22 (2H, m), 4.40 (1H, m), 5.89 (2H, s), 6.13 (1H, s), 6.66 (1H, d, J=7.8 Hz),J=7.8 Hz), 6.70–6.86 (4H, m), 6.96 (1H, d, J=2.2 Hz).

Reference Example 1

Recovery of (1S, 2R)-(+)-Norephedrine

The extracting operation in Example 2 Step 2 was carried out several times and 113 kg of the remaining aqueous layer was concentrated under reduced pressure to give 6240 g of (1S, 2R)-(+)-norephedrine phosphate. Into 25% aqueous solution of sodium hydroxide was poured 6240 g of the phosphate below 35° C. over 40 minutes and the solution was stirred for 2 hours.

The slurry of the reaction solution was filtered and the obtained crystals of sodium phosphate were washed with 39 L of toluene. The obtained filtrate was separated to remove an aqueous layer, a toluene layer was dried over sodium sulfate, concentrated under reduced pressure, diluted with 4 L of hexane, crystallized and filtered to give 3567 g of (1S, 2R)-(+)-norephedrine as white crystals.

$[\alpha]_D^{22}$+41.5 (c=5.0, N—HCl); mp 51° C.; Calcd. for C$_9$H$_{13}$NO: C, 71.49; H, 8.67; N, 9.26. Found: C, 71.38; H, 8.65; N, 9.26.

Example 3

Compound (III-1: racemate) (50 mg) and (R)-(+)-α-methylbenzylamine (16 mg) were added to a mixture of methanol (0.5 ml) and ethyl acetate (1.0 ml), and the solution was allowed to stand at room temperature for 3 days. The precipitates were filtered to give Compound (II-1: R-salt) (9 mg, R/S=99/1).

Example 4

Compound (III-1: racemate) (100 mg) and (1S, 2R)-(+)-norephedrine (39.3 mg) were dissolved in isopropylalcohol (1.8 ml) and the solution was allowed to stand at room temperature overnight. The precipitates were filtered to give Compound (II-1: R-salt) (53 mg, R/S=9317).

Example 5

Compound (III-1: racemate) (7.12 g) and cinchonine (5.45 g) was added in methanol (39 ml) and the slurry was stirred at 40° C. for 20 hours in a water bath for racemization and preferential crystallization. The slurry was cooled under ice-cooling and the obtained crystals were filtered and washed with cooled methanol to give 7.49 g of Compound (II-1: R-salt) (60%) (R/S=99.7/0.3).

Example 6

Compound (III-1: racemate) (1569 g) was added to a mixture of methanol (6.56 L) and (is, 2R)-(+)-norephedrine (617 g) to dissolve with heating. The solution was cooled to be slurry, which is stirred for 8 hours keeping at 45° C. for racemization and preferential recrystallization. After the slurry was cooled with ice, the precipitates were filtered and washed with cold methanol (3 L) to give 1175 g of Compound (II-1: R-salt) (54%) (R/S=98.2/1.8).

The filtrate (R/S=20/77) was racemized and subjected to optical resolution again.

Example 7

Compound (III-1: racemate) (50 mg) and quinidine (42.2 mg) were dissolved in a mixture of ethyl acetate (0.5 ml) and ethanol (0.5 ml) and the mixture was allowed to stand at room temperature overnight. The solution was concentrated and the residue was crystallized from ethyl acetate-ether. The crystals were filtered to give Compound (II-1: S-salt) (28 mg, R/S=4/96).

Example 8

Compound (III-1: racemate) (2.00 g) and (1S, 2R)-(+)-norephedrine (0.79 g) were dissolved in ethyl acetate (20 ml) and the mixture was allowed to stand at room temperature overnight. The precipitates were filtered to give Compound (II-1: R-salt) (1.33 g, R/S=95/5). A solution of the precipitates (1.33 g, R/S=95/5) in acetone (14.5 ml) was allowed to stand for 3 days. The precipitates were filtered to give Compound (II-1: R-salt) (0.90 g, R/S=99.5/0.5).

Retention time on the above HPLC analysis: 10.15 min (R), 11.37 min (S) mp 157° C. (decompose); $[\alpha]_D^{22}$+50.8±0.9 (c=1.0, MeOH); Calcd. for C$_{21}$H$_{20}$O$_7$·C$_9$H$_{13}$NO: C, 67.28; H, 6.21; N, 2.62; Found: C, 67.17; H, 6.25; N, 2.77.

Example 9

Compound (III-1: racemate) (327 g) and (1S, 2R)-(+)-norephedrine (128.6 g) were dissolved in ethyl acetate (3.27 L) and the solution was allowed to stand at room temperature overnight. The precipitates were filtered to give Compound (II-1: R-salt) (217 g, R/S=94/6) and the filtrate was concentrated to give 260 g of yellow residue (R/S=8/92). The obtained 217 g of crystals (II-1: R-salt, R/S=94/6) were dissolved in methanol (2.17 L) with heating, diluted with acetonitrile (2.17 L) and concentrated under reduced pressure to remove methanol. Acetonitrile (1.0 L) was added to the residue like slurry and the solution was concentrated again. The precipitates were filtered to give 184 g of Compound (II-1: R-salt) (40%, R/S=100/0). The filtrate was concentrated under reduced pressure to give 31 g of a residue (R/S=45/54).

Retention time on the above HPLC analysis: 10.15 min (R), 11.37 min (S) $[\alpha]_D{}^{22}$+51.0±0.9 (c=1.0, MeOH); Calcd. for $C_{21}H_{20}O_7 \cdot C_9H_{13}NO$: C, 67.28; H, 6.21; N, 2.62; Found: C, 67.25; H, 6.27; N, 2.91.

Example 10

Compound (III-1: racemate) (600 g) and (1S, 2R)-(+)-norephedrine (236 g) were dissolved in ethyl acetate (6 L) and the mixture was allowed to stand at room temperature overnight. The precipitates were filtered to give 391.8 g of Compound (II-1: R-salt) (R/S=96/4). The filtrate was concentrated to give 572 g of a yellow residue. (R/S=8/92). In methanol (4 L), 391.8 g of crystals of Compound (II-1: R-salt) was dissolved with heating and the solution was diluted with acetonitrile (3 L) and concentrated under reduced pressure. Acetonitrile (5 L) was added the residue like slurry and concentrated again to reduce the volume of the solution to 3.83 kg. After the solution was allowed to stand for 1.5 hours, the precipitate was filtered to give 350 g of Compound (II-1: R-salt) (42%) (R/S=100/0). The filtrate was concentrated to give 44 g of a residue (R/S=29/71).

$[\alpha]_D{}^{23.5}$+51.0±0.9 (c=1.0, MeOH); Calcd. for $C_{21}H_{20}O_7 \cdot C_9H_{13}NO$: C, 67.28; H, 6.21; N, 2.62; Found: C, 67.16; H, 6.32; N, 2.90.

Example 11

The obtained residue in Examples 9 and 10, total 907 g (R/S=11/89), was dissolved in methanol (6 L) and the solution was refluxed for 5.5 hours to racemization (R/S=48/51). Methanol was concentrated to reduce the volume to 3.21 kg and the residue was cooled with water for crystallization and filtered. The precipitates were washed with cold methanol (0.5 L) to give 251 g of (II-1: R-salt) (R/S=99/1). The obtained filtrate (R/S=21/77) was refluxed again for 4.5 hours to racemize (R/S=47/51).

The solution was concentrated and cooled with water. The precipitates were filtered and washed with cold methanol (0.7 L) to give 167 g of (II-1: R-salt) (R/S=92/8). The obtained filtrate resulted in R/S=19/77.

Industrial Applicability

Optically active Compound (II) can be easily obtained by the process of the present invention and Compound (I) and/or (α) which is useful as a medicament or intermediate thereof can efficiently be produced.

What is claimed is:
1. A crystalline salt of the formula (II):

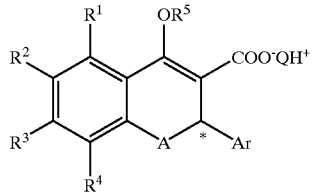

wherein * represents the position of an asymmetric carbon atom and that the compound is the (R) or (S) isomer and $R^1$, $R^2$, $R^3$ and $R^4$ are each independently hydrogen, hydroxy, halogen, optionally substituted alkyl wherein the substituent is halogen, hydroxy, cycloalkyl, carboxy, alkoxycarbonyl, alkoxy, alkoxyalkyloxy, acyl, alkylenedioxy, amino alkylamino, aryl or heterocyclyl optionally substituted alkenyl wherein the substituent is the same as the above,
optionally substituted alkynyl wherein the substituent is the same as the above,
optionally substituted cycloalkyl wherein the substituent is the same as the above,
optionally substituted alkoxy wherein the substituent is the same as the above,
optionally substituted alkenyloxy wherein the substituent is the same as the above,
optionally substituted alkynyloxy wherein the substituent is the same as the above,
optionally substituted cycloalkoxy wherein the substituent is alkyl, alkenyl, halogen, hydroxy, cycloalkyl, carboxy, alkoxycarbonyl, alkoxy, alkoxyalkyloxy, acyl, amino, alkylamino, alkylenedioxy, aryl or heterocyclyl,
optionally substituted acyloxy, wherein the substituent is halogen, hydroxy, cycloalkyl, carboxy, alkoxycarbonyl, alkoxy, alkoxyalkyloxy, acyl, alkylenedioxy, amino, alkylamino, aryl or heterocyclyl,
or optionally substituted amino wherein the substituent is alkyl,
cycloalkyl, aryl or acyl,
$R^5$ is alkyl or alkoxyalkyl,
A is O or S,
Ar is optionally substituted aryl wherein the substituent is alkyl, alkenyl, halogen, hydroxy, cycloalkyl, carboxy, alkoxycarbonyl, alkoxy, alkoxyalkyloxy, acyl, alkylenedioxy, amino, alkylamino, aryl or heterocyclyl, and Q represents an optically active compound.
2. The compound of claim 1, wherein Q is selected from the group consisting of norephedrine, 1-methylbenzylamine, cinchonine and quinidine, wherein the point of attachment to the structure is through the amino group.

* * * * *